United States Patent [19]

Dolhyj et al.

[11] 4,140,690

[45] Feb. 20, 1979

[54] PROCESS FOR PRODUCING PYRIDINE OR A SUBSTITUTED PYRIDINE BY AMMOXIDATION OF TERPENES

[75] Inventors: Serge R. Dolhyj, Parma; Louis J. Velenyi, Lyndhurst, both of Ohio

[73] Assignee: The Standard Oil Company, Cleveland, Ohio

[21] Appl. No.: 790,115

[22] Filed: Apr. 22, 1977

[51] Int. Cl.$^2$ .......................................... C07D 213/16
[52] U.S. Cl. .................. 546/253; 260/313.1; 260/333; 260/592; 568/826; 568/687; 252/456; 252/458; 252/459; 252/464
[58] Field of Search ..................................... 260/290 P

[56] References Cited

U.S. PATENT DOCUMENTS

| | | |
|---|---|---|
| 2,863,882 | 12/1958 | Bain et al. .......................... 260/348.5 |
| 3,014,047 | 12/1961 | Bain et al. ............................ 260/348 |

*Primary Examiner*—Alan L. Rotman
*Attorney, Agent, or Firm*—Herbert D. Knudsen; William D. Mooney

[57] ABSTRACT

Terpenes are oxidized by contacting the terpene and oxygen with a catalyst. The catalyst may be either (a) a bismuth molybdate or (b) antimony oxide containing iron oxide and/or uranium oxide.

3 Claims, No Drawings

PROCESS FOR PRODUCING PYRIDINE OR A SUBSTITUTED PYRIDINE BY AMMOXIDATION OF TERPENES

BACKGROUND OF THE INVENTION

The present invention relates to a novel method for oxidizing terpenes to form various useful products.

Techniques for oxidizing various terpenes such as limonene and the like to form useful products are well known. See, for example, U.S. Pat. No. 3,014,047, the disclosure of which is incorporated herein by reference. Unfortunately, the capability of known processes to produce desired end products in high yields with high selectivities is relatively low.

Accordingly, it is an object of the present invention to provide a novel process for oxidizing terpenes to useful products which can be accomplished with high conversion efficiencies and high selectivities to the desired end products.

SUMMARY OF THE INVENTION

These and other objects are accomplished by the present invention in accordance with which terpenes are oxidized in the presence of specific oxidation catalysts. In particular, the present invention in one embodiment contemplates that the oxidation catalysts employed are oxide complexes based on bismuth and molybdenum while in another embodiment the present invention contemplates that the oxidation catalysts employed are oxide complexes based on antimony and uranium or antimony and iron. By contacting the terpene to be oxidized with air or other oxygen-containing gas in the presence of one of these catalysts, it has been found that the objective products can be produced with significantly higher selectivities and conversions than obtainable in prior art processes.

DETAILED DESCRIPTION

In general, the inventive process comprises contacting a mixture of the terpene to be oxidized and oxygen with an oxidation catalyst in a reaction zone. The reaction may be accomplished either in the liquid phase or the vapor phase either in batch mode or continuously.

In accordance with the present invention, any terpene or terpene derivative can be oxidized to yield useful products. Preferably, however, the terpenes employed are those which are characterized as members of the p-menthane series and possessing a single ring double bond at the 1-2 position. Examples of useful terpenes are limonene, terpinoline, $\gamma$-terpinene, $\alpha$-terpinene, $\beta$-thellandrine, $\alpha$-thellandrene, isoterpinole and 3,8(9) p-menthadiene.

In carrying out the inventive process, any gas containing elemental oxygen can be employed. Preferably, however, air is employed since it is least expensive.

The temperature of the reaction should be adjusted so as to promote the formation of the desired product. In this connection it has been found that if the reaction temperature is too high, the reaction product obtained will contain mostly waste. Therefore, care must be taken to keep the reaction temperature below a value at which waste is predominantly formed. The specific maximum temperature in a particular embodiment of the invention varies depending upon the starting material and the catalyst and can be determined very simply by routine experimentation. Also, the reaction temperature should be high enough so that significant conversion of the starting material occurs. Generally, it has been found that when the process is carried out in the liquid phase, the reaction temperature should be between room temperature and 250° C., preferably between 90° and 200° C. at atmospheric pressure. When the reaction is carried out in the gas phase, however, the reaction temperature is normally somewhat higher, generally about 200°-500° C., preferably 200°-300° C. with contact time between about 0.1-10 seconds, preferably 0.5-3 seconds. The reaction temperature may vary somewhat depending upon the reaction pressure and the contact time (when the reaction is carried out in the gas phase), and these variables can be easily determined by one skilled in the art through routine experimentation.

The terpene/oxygen mixture is contacted with the catalyst for time sufficient to effect conversion of the terpene to the desired end product but insufficient to cause conversion of the terpene to significant waste. Generally this can be best determined by routine experimentation and is different depending upon the catalyst or the starting material employed. As a general guide, however, it has been found that when the reaction is carried out in the gas phase, contact times of between about 0.1 and 10 seconds, preferably 0.5 to 2 seconds, and optimally about one second, are effective. On the other hand, when the reaction is carried out in the liquid phase, reaction times on the order of 1 to 24 hours, preferably 2 to 7 hours, have been found useful.

It has also been found beneficial to add a diluent to the reaction when carried out in a gas phase. The diluent serves to decrease exotherms and thereby controls the reaction temperature. Any inert gas such as nitrogen, $CO_2$ can be used as the diluent. Water is a preferred diluent. When the reaction is carried out in the liquid phase, a solvent for the reactants and products can be included in the reaction system. In the liquid phase reaction a solvent serves to control reaction temperature at a specific reflux condition and also serves as a diluent. Examples of compounds which are useful as solvents are saturated hydrocarbons, benzene, alkylbenzenes, cyclohexane, etc.

The catalysts employed in the inventive process can be generally described as one of two types. One type of catalyst is a bismuth molybdate type catalyst or bismuth phosphomolybdate catalyst while the other type of catalyst is an antimony oxide/iron oxide or antimony oxide/uranium oxide type catalyst. Both types of catalysts are characterized as oxide complexes and are well known in the art of oxidation catalysis.

Bismuth molybdate catalysts are described inter alia in the following patents: U.S. Pat. Nos. 2,904,580, 3,044,966, 3,186,955, 3,248,340, 3,576,764, 3,629,148, 3,642,930, and 3,803,204.

Antimony oxide catalysts further containing iron oxide and/or uranium oxide are described in the following patents: U.S. Pat. Nos. 3,197,419, 3,198,750, 3,308,151, 3,328,315, 3,409,697, 3,431,292, 3,445,521, 3,468,958, and 3,546,138. The disclosures of all of these patents are incorporated herein by reference.

In carrying out the inventive process, any of the oxide complex catalysts disclosed in these patents can be employed in each of the different embodiments of the inventive process. Preferred catalysts have the following compositions:

82.5% $K_{0.05}Ni_{2.5}Co_{4.5}Fe_3BiP_{0.5}Mo_{12}O_x$ — 17.5% $SiO_2$

100% $USb_{4.6}O_x$
50% $Bi_9PMo_{12}O_x$ — 50% $SiO_2$
82.5% $FeSb_{8.6}O_x$ — 17.5% $SiO_2$
50% $Cs_{0.05}K_{0.1}Ni_{2.5}Co_{4.5}Fe_2MnBiCr_{0.5}Mo_{12.6}O_x$.50% $SiO_2$

The reaction products produced by the inventive process vary depending upon whether the process is carried out in the gas phase or in the liquid phase. The predominant products of the liquid phase reaction are ketones, aldehydes, alcohols, epoxides and products resulting from isomerization and dehydrogenation of the starting materials. For example, the product obtained upon the liquid phase oxidation of d-limonene contains pulegone, 1-p-menthen-9-al, dihydrocarvone, carvone, carveol, dipentene oxide, α-terpineol, carvacrol, α-terpinene, 2,4(8)-p-menthadiene, 1,4(8)-p-menthadiene, cymene (ortho, meta and para), and α-methyl acetophenone. These products can be recovered by conventional techniques as discussed in U.S. Pat. No. 3,014,047 and are useful as flavoring agents, perfume ingredients and constituents of various pharmaceutical preparations. Also, pulegone can be transformed to menthol (which enjoys wide commercial use in perfumery, flavorings, confectionaries and pharmaceuticals) by hydrogenation of the pulegone in accordance with conventional techniques for hydrogenation of unsaturated ketones.

When the reaction is carried out in the vapor phase, isomerization and dehydrogenation products are predominantly obtained. For example, when d-limonene is oxidized in the liquid phase, the predominant product is cymene. Cymene and its derivatives find uses as solvents, ingredients of metal polishes, starting materials for hydroperoxide initiators for use in synthetic rubber manufacture and the like. Also, cymene can be readily converted to paracresol by well-known techniques.

Alternate Embodiment

In another embodiment of the present invention, it has been found that terpenes can be ammoxidized in the gas phase to give substituted pyridines as reaction products. The gas phase ammoxidation reaction of this embodiment is carried out in essentially the same way and under the same conditions as the gas phase oxidation reaction discussed above. However, in the ammoxidation reaction, ammonia is added to the terpene/oxygen mixture, the ammonia being present in an amount of 0.1 to 10, preferably 0.5 to 2, mole % with respect to the oxygen content of the feed mixture. As is well known, substituted pyridines such as 2,4,6-trimethyl pyridine find uses as solvents, chemical intermediates and dehydrohalogenating agents.

Working Examples

In order to provide a better understanding of the present invention, the following working examples are presented:

Liquid Phase

A number of experiments were conducted with the reactant being in the liquid phase. In one set of experiments, the reaction was performed under pressure in an autoclave while in another set of experiments, the reaction was carried out in the liquid phase at atmospheric pressure.

The experiments carried out under pressure were conducted in a Parr autoclave. In one set of experiments, 20 grams d-limonene, 100 grams toluene as a solvent and 3 grams catalyst (less than 50 mesh) were placed in the glass liner of the autoclave and the apparatus assembled. Next, the apparatus was pressurized with air to a pressure of 65 psig. The reaction was carried out at 175° C. for 2 hours. After cooling, the pressure was released and the catalyst and liquid were separated from one another by filtration.

In another similar experiment, the same procedure was used except that the autoclave was initially charged with air to a pressure of 190 psig. After an hour and a half, a gas sample was taken and the pressure was released. Then the reaction vessel was recharged with air to 160 psig and the reaction continued for two hours. A gas sample was taken and the recharging steps were repeated. After one more hour, the reaction was stopped and the final gas sample was collected followed by separation of the liquid and catalysts.

Those experiments carried out at atmospheric pressure were conducted in a round bottom flask equipped with a water cooler, a condenser, a thermometer and a set-up for introducing gases under the liquid surface. This set-up included pressure regulators on the gas cylinders, valves for controlling the gas flow and ⅛" stainless steel lines. When two feed gases were used, the two streams were combined in a T before entering the solution.

In a typical experiment, 20 grams d-limonene, solvent (benzene) in an amount of 50% with respective limonene and 2.5 grams catalyst (less than 50 mesh) were placed in the round bottom flask and the apparatus was assembled as described above. The reaction took place with constant stirring at 90° C. while air was bubbled through the liquid. After a suitable period of time, the reaction was cooled and the catalyst was separated by filtration.

The following experiments 1 to 9 were conducted in this manner. The experiments are summarized in the following Table I. In this and following tables catalyst designations "V", "W", "X", "Y" and "Z" have the following meanings:

| Designation | Catalyst Composition |
|---|---|
| W | 82.5% $FeSb_{8.6}O_x$ 17.5% $SiO_2$ |
| X | 82.5% $K_{0.05}Ni_{2.5}Co_{4.5}Fe_3BiP_{0.5}Mo_{12}O_x$ 17.5% $SiO_2$ |
| Y | 100% $USb_{4.6}O_x$ |
| Z | 50% $Bi_9PMo_{12}O_x$ 50% $SiO_2$ |
| V | 50% $Cs_{0.05}K_{0.1}Ni_{2.5}Co_{4.5}Fe_2MnBiCr_{0.5}Mo_{12.6}O_x$.50% $SiO_2$ |

TABLE I

| | | SUMMARY OF RUNS IN LIQUID PHASE | | | | | | | | |
|---|---|---|---|---|---|---|---|---|---|---|
| | Example | 1 | 2 | 3 | 4 | 5 | 6 | 7 | 8 | 9 |
| Reaction | Cat | None | X | X | X | X | X | X | X | V |
| | Temp | 90° C | 90° C | 144° C | 170° C | 95° C | 150° C | 118° C | 182° C | 140° C |
| | Time | 5½ hrs | 5½ hrs | 6¼ hrs | 2 hrs | 4½ hrs | 3 hrs | 4½ hrs | 4¾ hrs | 6½ hrs |
| | Gases | air | air | air | air | air | $O_2$ | $NH_3$, $O_2$ | $NH_3$, $O_2$ | $O_2$ |
| PRODUCTS | | | | | | | | | | |
| Unreacted hydrocarbon | | 83.03 | 67.63 | 39.06 | 64.26 | 49.07 | 56.61 | 45.45 | 89.90 | 58.95 |
| Isoprene | | | | | 0.84 | | | | | 0.28 |

TABLE I-continued
SUMMARY OF RUNS IN LIQUID PHASE

| Example | 1 | 2 | 3 | 4 | 5 | 6 | 7 | 8 | 9 |
|---|---|---|---|---|---|---|---|---|---|
| Reaction Cat | None | X | X | X | X | X | X | X | V |
| Temp | 90° C | 90° C | 144° C | 170° C | 150° C | 95° C | 118° C | 182° C | 140° C |
| Time | 5½ hrs | 5½ hrs | 6¼ hrs | 2 hrs | 4½ hrs | 3 hrs | 4½ hrs | 4¾ hrs | 6¼ hrs |
| Gases | air | air | air | air | air | $O_2$ | $NH_3$, $O_2$ | $NH_3$, $O_2$ | $O_2$ |
| PRODUCTS | | | | | | | | | |
| Butylbenzene | 0.98 | 1.87 | | | | | | 1.91 | |
| Isomer of limonene | | | 3.02 | 16.37 | 8.28 | 1.62 | | | 7.02 |
| Cymene | 1.00 | 2.92 | 3.99 | 10.56 | 1.93 | 4.81 | 1.90 | 0.94 | 27.96 |
| $C_{10}H_{12}$ | 2.72 | 8.72 | 3.72 | 3.48 | 4.89 | 4.15 | 17.37 | 0.57 | 2.89 |
| Pulegone | 1.63 | 3.87 | 3.07 | | 4.34 | 2.32 | 13.50 | | 0.58 |
| p-menthane-9-al | 0.88 | 1.49 | 8.43 | | | | | | |
| Menthenol | 0.50 | 0.74 | 2.93 | 0.34 | 0.75 | 2.06 | 5.70 | | |
| Dihydrocarvone | 0.38 | 0.79 | 9.06 | 0.86 | 7.76 | 8.76 | 2.54 | 1.13 | 0.91 |
| α-terpineol | | | 4.36 | 0.46 | 2.99 | 2.96 | | | 0.44 |
| 1-octene | | | | | | | 1.67 | | |
| 1-octanol | | | | | | | | 2.90 | |
| Menthenol | | | | 0.31 | 1.17 | 0.44 | | | |
| Carvacrol | | | | | 0.60 | 0.70 | 0.21 | | |
| Carvone | 1.67 | 0.80 | 8.57 | 0.29 | 3.47 | 11.14 | 3.66 | 2.67 | 0.23 |
| α-methylacetophenone | | 0.29 | 2.67 | 0.23 | 2.20 | 3.68 | 0.41 | | 0.10 |
| Carveol | | | 4.07 | | | | | | |
| $C_{10}H_{16}O$ | 1.19 | 1.43 | | 0.25 | 1.32 | | 3.30 | | 0.15 |
| $C_{10}H_{14}O$ | 0.69 | 1.20 | 1.02 | 0.25 | 1.26 | | 1.34 | | |
| $C_{10}H_{12}O$ | | 0.13 | 0.63 | 0.23 | | | 1.24 | | |
| Dipentene oxide | | | 2.53 | | | | | | |
| Unidentified (combined) | 4.85 | 3.66 | 2.85 | 1.28 | 9.98 | 0.73 | 1.71 | | 0.50 |

Gas Phase

Additional experiments were conducted with the reaction being carried out in the gas phase. In these experiments, d-limonene was oxidized in a 40 cc. fixed-bed reactor comprising a ¾″ × 0.095″ W.T. (1.9 cm. × 0.241 W.T.) Tube having an internal volume of 40 cc. The liquid d-limonene feed was pumped directly into the reactor. The upper part of the reactor was packed with 10 cc of 10/30 mesh inert Alundum packing which served as an evaporation zone. The lower 30 cc's of volume of the reactor was packed with catalyst. Usually, 10/30 mesh catalyst particles were used. Steam, if used, was generated by passing liquid water through a stainless steel evaporation block kept at 200° C.+. The liquid hydrocarbon and water were pumped by calibrated "Sage" syringe pumps, while air was supplied by calibrated rotometer. The exit gases were scrubbed out in acetone traps at 0° C. then analyzed for $O_2$, $N_2$, CO and $CO_2$ using a Carle gas chromatograph equipped with a parallel column system. The liquid in the acetone scrubber were analyzed by an H-P chromatograph with an FID detector equipped with a 16 foot, 20 M carbowax column-20% (GC #1, col "A"). D-limonene was used as a standard to determine the concentration of other components. The column was normally programmed from 85° C. (8 minutes hold) to 170° C. (at 32° C. per minute). The identity of significant product species was determined by a combined gas chromatographic/mass spectrographic technique.

The results obtained are set forth in the following Table II.

TABLE II
SUMMARY OF RUNS IN GAS PHASE

| Example No. | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|
| Cat. | X | X | X | X | X | X | X | Y | Y | Y | Z | Z | W | W | W |
| Temp. Reac.° C | 200 | 225 | 225 | 250 | 275 | 300 | 350 | 300 | 350 | 400 | 350 | 325 | 325 | 350 | 375 |
| Temp. Exo.° C | 234 | 265 | 236 | 265 | 295 | 328 | 475 | 310 | 365 | 530 | 415 | 361 | 344 | 378 | 540 |
| Contact Time, Seconds | 2 | 2 | 1 | 1 | 1 | 1 | 1 | 1 | 1 | 1 | 1 | 1 | | 1 | 1 |
| Catalyst Vol. cc | 30 | 30 | 30 | 30 | 30 | 30 | 30 | 30 | 30 | 30 | 30 | 30 | 30 | 30 | 30 |
| Feed Gas Mole Ratios | | | | | | | | | | | | | | | |
| HC | 1 | 1 | 1 | 1 | 1 | 1 | 1 | 1 | 1 | 1 | 1 | 1 | 1 | 1 | 1 |
| Air | 20 | 20 | 20 | 20 | 20 | 20 | 20 | 20 | 20 | 20 | 20 | 20 | 20 | 20 | 20 |
| $N_2$ | 0 | 0 | 0 | 0 | 0 | 0 | 0 | 0 | 0 | 0 | 0 | 0 | 0 | 0 | 0 |
| $H_2O$ | 0 | 0 | 20 | 20 | 20 | 20 | 20 | 20 | 20 | 20 | 20 | 20 | 20 | 20 | 20 |
| Per Pass Conversion % C | | | | | | | | | | | | | | | |
| CO | 0.3 | 22.3 | 0 | 0 | 0.4 | 0.6 | 7.6 | 0.4 | 0.7 | 12.0 | 4.9 | 1.0 | 0.6 | 0.6 | 3.7 |
| $CO_2$ | 0.7 | 18.9 | 1.0 | 0.7 | 1.1 | 2.1 | 28.7 | 0.9 | 1.7 | 22.8 | 19.2 | 4.3 | 1.7 | 1.9 | 9.2 |
| 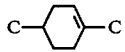 | 10.6 | | | | | | | | | | | | | | |
| d-limonene | 37.2 | 4.5 | 41.2 | 26.0 | 17.1 | 9.0 | 2.4 | 92.6 | 87.4 | 15.9 | 7.1 | | 78.6 | 77.9 | 76.4 |
| isoprene | | 28.9 | | | | | | | | 45.7 | 5.7 | | 3.7 | 2.0 | 2.7 |
| cymene | 47.8 | 17.7 | 44.8 | 55.8 | 61.2 | 72.5 | 47.2 | 3.9 | 5.8 | | 49.0 | 86.1 | 10.6 | 8.4 | |
| $C_{10}H_{14}$ aromatic | | | 9.4 | 12.0 | 13.1 | 6.8 | | | | | | | | | |
| $C_{10}H_{12}$ allyl toluene | 3.4 | 7.7 | 3.6 | 5.4 | 7.3 | 9.0 | 10.1 | 2.2 | 4.5 | 3.6 | 7.1 | 8.6 | 4.8 | 7.9 | 8.0 |
| unknowns | | | | | | | | | | | | | | | |
| % Selectivity | | | | | | 4.0 | | | | | | 6.9 | | | 1.2 |
| C—⌬—C | 16.9 | | | | | | | | | | | | | | |

TABLE II-continued
SUMMARY OF RUNS IN GAS PHASE

| Example No. | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|
| Cat. | X | X | X | X | X | X | X | Y | Y | Y | Z | Z | W | W | W |
| d-limonene | | | | | | | | | | | | | | | |
| isoprene | | | | | | | | | | | | | | | |
| cymene | | 18.5 | | | | 79.7 | 48.4 | 52.7 | 46.0 | | 52.7 | 86.1 | | | |
| $C_{10}H_{14}$ | | | | | | 7.5 | | | | | | | | | |
| aromatics | | | | | | | | | | | | | | | |
| $C_{10}H_{12}$ | 5.4 | 8.1 | 6.1 | 7.3 | 8.8 | 9.9 | 10.3 | 29.7 | 35.7 | 4.3 | | 8.6 | 22.4 | 35.7 | 33.9 |
| allyl toluene | | | | | | | | | | | | | | | |

Additional Embodiment - Ammoxidation

As indicated above, it has also been found that terpenes can be ammoxidized with the previously discussed catalysts to useful products. For example, ammoxidation of limonene yields trimethylpyridine. Other analogous reaction products such as other substituted pyridines such as alkyl substituted pyridines and substituted pyrroles are produced by the ammoxidation of corresponding terpene compounds depending on location of double bonds in the system.

In order to further illustrate this embodiment of the present invention, a number of working examples were carried out. These ammoxidation reactions were conducted in the gas phase with a 20 cc fixed-bed reactor. The reactor comprises ½" × 0.049" W.T. (1.27 cm. × 0.124 cm. W.T.) Tube having internal volume of 20 cc. The top of the reactor was packed with an inert material, 10 mesh Alundum and then charged with 10/30 mesh catalysts. D-limonene was fed by a Sage pump equipped with a glass syringe. The pump was callibrated prior to the runs. The product samples were collected in acetone cooled by ice-water. Tail gas samples were also collected during the runs. When $NH_3$ was used, it was necessary to scrub the tail gas by bubbling it through an HCl solution. The products were analyzed by the gas chromatography and the identity of products were confirmed by combined GC/MAS-SPEC analysis.

The results of these experiments are set forth in the following Table III.

Although only a few embodiments of the present invention have been described above, it should be appreciated that many modifications can be made without departing from the spirit and scope of the invention. All such modifications are intended to be included within the scope of the present invention, which is to be limited only by the following claims.

We claim:

1. A gas phase process for producing pyridine or a substituted pyridine by ammoxidizing a terpene comprising contacting said terpene, oxygen and ammonia in a reaction zone with a catalyst selected from the group consisting of
   a. a catalytically active complex oxide of bismuth and molybdenum, and
   b. a catalytically active complex oxide of antimony oxide containing at least one of iron oxide and uranium oxide.

2. The process of claim 1 wherein said complex oxide of bismuth and molybdenum contains about 0.1–12 atoms of bismuth for each 0.1–12 atoms of molybdenum and enough oxygen to satisfy the valence requirements of the other elements present; and wherein said complex oxide of antimony oxide containing at least one of iron oxide and uranium oxide contains 1–99 atoms of antimony for each 50–1 atoms of iron and each 50–1 atoms of uranium and enough oxygen to satisfy the valence requirements of the other elements present.

3. The process of claim 1 wherein said terpene is limonene.

* * * * *

TABLE III
SUMMARY OF AMMOXIDATION RUNS
20 CC FIXED BED REACTOR

| | Temp. of | | Ratio | C.T. | Per Pass Conversions % C | | | | | | | | Hours on | Catalyst |
|---|---|---|---|---|---|---|---|---|---|---|---|---|---|---|
| Ex. | Bath | Reac. | Air/HC/$NH_3$ | Sec. | Isoprene | Cymene | triMe py | $C_{10}H_{12}$ | CO | $CO_2$ | Unr. HC | Other | Stream | No. |
| 25 | 276 | 280 | 20/1/4 | 2 | 4.81 | 1.08 | 17.81 | 1.86 | 0 | 0.30 | 73.60 | 0.54 | 0.6 | X |
| 26 | 300 | 302 | 20/1/4 | 2 | 4.28 | 0.90 | 14.18 | 3.69 | 0.24 | 0.49 | 75.73 | 0.49 | 1.5 | X |
| 27 | 325 | 350 | 20/1/4 | 2 | 5.81 | 2.41 | 11.42 | 9.75 | 0.32 | 0.46 | 68.40) | 1.41 | 2.1 | X |
| 28 | 350 | 359 | 20/1/4 | 2 | 6.20 | 4.16 | 21.51 | 22.56 | 0.76 | 0.70 | 41.00 | 3.10 | 2.9 | X |
| 29 | 375 | 376 | 20/1/4 | 2 | 11.22 | 14.24 | 31.91 | 29.23 | 1.58 | 1.46 | 5.83 | | 0.9 | X |
| 30 | 400 | 412 | 20/1/4 | 2 | 8.55 | 2.66 | 13.31 | 20.02 | 2.68 | 0.82 | 51.96 | | 0.8 | W |
| 31 | 420 | 438 | 20/1/4 | 2 | 9.51 | 1.31 | 23.32 | 20.12 | 3.85 | 1.42 | 40.47 | | 1.6 | W |
| 32 | 354 | 357 | 20/1/4 | 2 | 11.20 | 16.53 | 30.32 | 28.20 | 1.82 | 2.80 | 9.12 | | 1.9 | Z |
| 33 | 399 | 408 | 20/1/4 | 2 | 4.16 | 31.85 | 5.57 | 31.88 | 2.48 | 10.38 | 7.01 | 6.67 | 1.0 | Z |
| 34 | 350 | 352 | 20/1/4 | 2 | 6.42 | 1.57 | 10.06 | 3.90 | 0.61 | 0.72 | 76.70 | | 0.7 | Y |
| 35 | 400 | 406 | 20/1/4 | 2 | 8.39 | 1.26 | 8.40 | 9.08 | 2.09 | 0.70 | 70.09 | | 0.8 | Y |
| 36 | 426 | 428 | 2/1/4 | 2 | 10.67 | 0.42 | 6.87 | 9.94 | 3.44 | 2.44 | 66.23 | | 2.1 | Y |